United States Patent [19]

Brändström et al.

[11] Patent Number: 4,544,750

[45] Date of Patent: Oct. 1, 1985

[54] CERTAIN PYRIDYL-N-OXIDE INTERMEDIATES FOR THE PREPARATION OF OMEPRAZOLE

[75] Inventors: Arne E. Brändström; Bo R. Lamm, both of Göteborg, Sweden

[73] Assignee: Aktiebolaget Hassle, Molndal, Sweden

[21] Appl. No.: 526,900

[22] Filed: Aug. 26, 1983

[30] Foreign Application Priority Data

Aug. 26, 1982 [SE] Sweden .............................. 8204879

[51] Int. Cl.[4] .......................................... C07D 213/68
[52] U.S. Cl. .................................. 546/290; 546/347
[58] Field of Search ........................................ 546/290

[56] References Cited

U.S. PATENT DOCUMENTS

| | | | |
|---|---|---|---|
| 2,663,711 | 12/1953 | Bullitt ................................ | 546/344 |
| 2,735,851 | 2/1956 | Cislak ................................ | 546/344 |
| 4,215,126 | 7/1980 | Durant et al. ..................... | 424/263 |
| 4,255,431 | 3/1981 | Junggren et al. ................. | 424/263 |
| 4,337,257 | 6/1982 | Junggren et al. ................. | 424/263 |

FOREIGN PATENT DOCUMENTS 0080602  6/1983  European Pat. Off. ............ 424/263

*Primary Examiner*—Alan L. Rotman
*Attorney, Agent, or Firm*—Brumbaugh, Graves, Donohue & Raymond

[57] ABSTRACT

Novel compounds of the formula

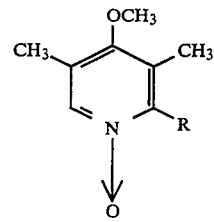

wherein R is H or $CH_3$, a process for their preparation, and their use as intermediates in the preparation of pharmaceutically useful compounds, e.g. substituted benzimidazoles containing a pyridine radical, i.a. omeprazole.

3 Claims, No Drawings

CERTAIN PYRIDYL-N-OXIDE INTERMEDIATES FOR THE PREPARATION OF OMEPRAZOLE

DESCRIPTION

1. Field of the Invention

The present invention relates to novel chemical intermediates, a process for their preparation, and their use in the preparation of pharmacologically active substances.

2. Background of the Invention

Compounds of the general formula (i) wherein $R^1$ and $R^2$ are the same or different and are each selected from the group consisting of hydrogen, alkyl, halogen, carbomethoxy, alkoxy and alkanoyl have been disclosed in e.g. European Pat. No. 0005 129 as useful therapeutical compounds. One of these compounds, known under the generic name omeprazole ($R^1=5-OCH_3$, $R^2=H$)

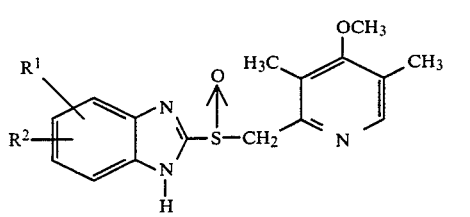

is being developed as a gastric acid secretion inhibiting drug. It can also be used for providing gastrointestinal cytoprotective effects in mammals and man.

It is important to obtain simple and efficient intermediates and routes of synthesis for omeprazole and, in a more general sense, for therapeutically active compounds such as benzimidazole derivatives containing the pyridylmethyl moiety

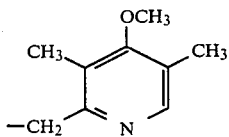

The present invention provides novel compounds which are useful as intermediates in the preparation of therapeutically active comounds such as benzimidazole derivatives which contain a pyridylmethyl radical of the formula (ii), and methods for the preparation of such compounds.

3. Prior Art

Substituted benzimidazoles containing a pyridine radical of the formula (ii) are disclosed i.a. in European Pat. No. 0005 129. A problem with these compounds is their stability characteristics. Upon storage without any special precautions being taken, they are degraded at a rate which is higher than desired. E.g. by storage of omeprazole, which is a substituted benzimidazole disclosed in the patent cited above, at accelerated conditions, that is at +37° C. and at a relative humidity of 80% for a period of 6 months, about 6% of the substance is converted to degradation products.

DETAILED DESCRIPTION OF THE INVENTION

It has been found according to the present invention that the compounds of the formula

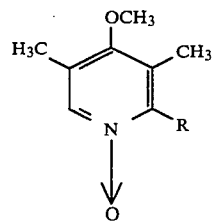

wherein R is H or $CH_3$, are novel and useful intermediates in the preparation of pharmaceutically useful compounds, e.g. substituted benzimidazoles of the general formula (i). The compounds of the formula I are the products obtained from the preceding nitration reaction (see preparation below), for which the N-oxide form may be considered necessary, and the following substitution reaction in which the pyridine N-oxide form is very advantageous considering the yields.

In addition, the N-oxide state of the compounds of the formula I is very advantageous for the subsequent conversion to the 2-hydroxymethyl-pyridine (procedures A and B). Direct hydroxymethylation of the corresponding non-oxidized pyridines

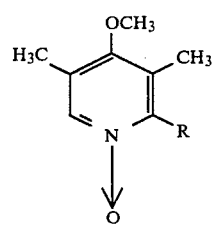

only gives low yields (<20%).

The compounds of the formula I may advantageously be prepared by processing both the nitration step and the substitution step without isolation of the intermediate nitro-pyridine. Furthermore they are stable and can be stored in bulk form. For example, the compounds according to the invention of the formula I are useful as intermediates in the preparation of the corresponding 2-hydroxymethylpyridine and reactive derivatives thereof of the formula

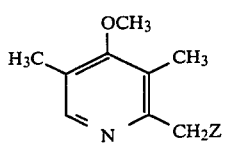

or a salt thereof, in which formula Z is a hydroxy group or reactive esterified hydroxy group, e.g. halogen such as Cl and p-toluenesulfonyl used for the preparation of e.g. omeprazole. The reactive intermediate of the formula (iii) is then reacted in known manner with a benzimidazole derivative of the formula

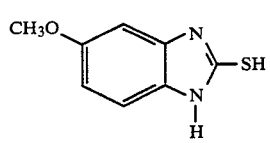

whereafter oxidation in known manner of the reaction product of the formula

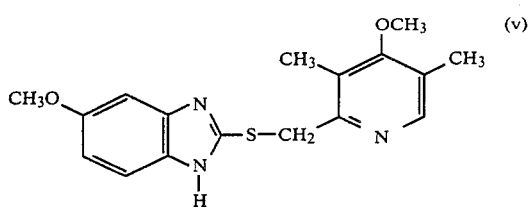

yields omeprazole. A preferable method of preparing omeprazole is to use a compound with the general formula I, wherein R is H as an intermediate. The most preferable method of preparing omeprazole is to use a compound, wherein R is CH₃ as an intermediate.

The present invention also relates to a process for the preparation of the compounds of the formula I.

The compounds of the invention of the formula I are prepared according to the invention by (a) reacting a compound of the formula

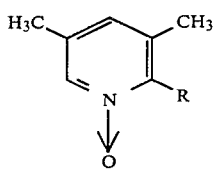

wherein R is H or CH₃, with a nitrating agent such as nitric acid

HNO₃     III to the formation of a compound of the formula

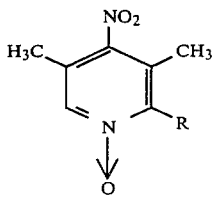

wherein R has the meaning given above whereafter (b) the compound of the formula IV is directly reacted with methoxide to give the desired end product of the formula

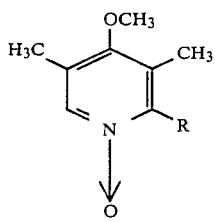

wherein R is H or CH₃.

The reaction conditions for the steps (a) and (b) are suitably the following.

For reaction (a), ordinary nitration conditions, i.e., a mixture of conc. sulfuric acid and nitric acid of different concentrations are used. Mixtures containing organic solvents such as acetic acid and nitromethane may also be used.

For reaction (b) a solution of methoxide anion in methanol is preferably used. Methoxide salts in inert solvents such as toluene may also be used. A solution of methoxide in methanol can be prepared from sodium hydroxide and methanol.

The utilization of the compounds I in the preparation of reactive derivatives of corresponding 2-hydroxymethylpyridine can be carried out as illustrated below;

A. Procedure useful for the preparation of a compound of the formula (iii) utilizing a compound of the formula I wherein R is CH₃:

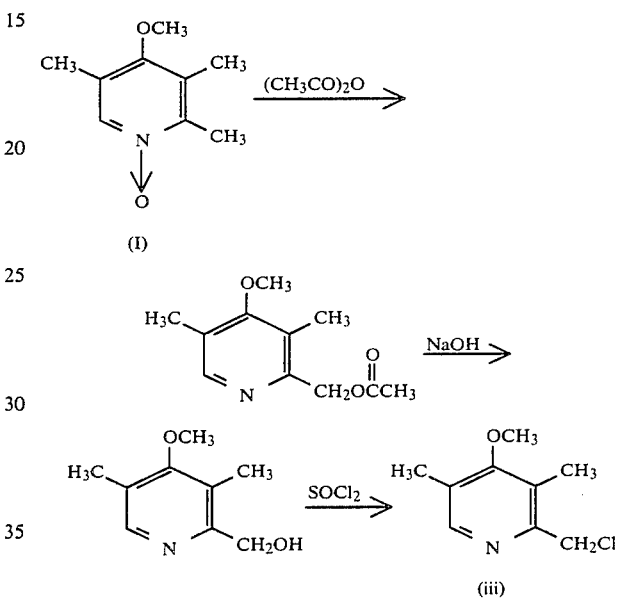

B. Procedure useful for the preparation of a compound of the formula (iii) utilizing a compound of the formula I wherein R is H:

Suitable sources of free radicals are e.g. $(NH_4)_2S_2O_8$ or other salts of persulfuric acid.

The compound of the formula (iii) thus obtained, or a salt thereof, is thereafter in known manner as described in the prior art reacted with the desired benzimidazole derivative (iv) as described above.

The invention is illustrated by the following examples.

EXAMPLE 1

Preparation of 2,3,5-trimethyl-4-methoxypyridine-N-oxide 2,3,5-trimethyl-pyridine-N-oxide (1457 g, 10 moles) was dissolved in conc. $H_2SO_4$ (1200 ml, 22.08 moles) in a 50 liters reaction vessel. A nitration solution (1750 ml, 32.2 moles conc. $H_2SO_4$ and 2065 ml, 29.84 moles 65% $HNO_3$) was added at 90° C. during 1 hour. The solution was stirred at 90° for 1.5 hours and thereafter cooled to 30° C. The pH of the reaction mixture was then adjusted by adding 10M NaOH (11.65 liters, 116.5 moles) during cooling with water so that the temperature was kept below 40° C. The NaOH was added during about 2 hours. Thereafter $CH_2Cl_2$ (25 liters) was added and the mixture stirred vigorously for 30 minutes. The phases formed were separated and the $CH_2Cl_2$-phase was transferred to a 100 liters reaction vessel. The water phase was discarded. The methylenechloride was distilled off. To the remainder was added 15 l of toluene which was then distilled off under reduced pressure, followed by another 15 l portion of toluene which was also removed by distillation. 8 liters of methanol was added and the mixture heated to boiling temperature. A solution of NaOH (595 g, 14.9 moles) in $CH_3OH$ (16 liters) was added during about 1.5 hours. The reaction mixture obtained was cooled and its pH adjusted to 8 using conc. $H_2SO_4$ (250 ml, 4.6 moles). Remaining methanol was distilled off and $CH_2Cl_2$ (20 liters) was added to the remainder. The mixture was stirred for about 30 minutes and inorganic salts were filtered off and washed with $CH_2Cl_2$. The filtrates obtained were pooled and evaporated, yielding 1287 g of 2,3,5-trimethyl-4-methoxy-pyridine-N-oxide with a purity of 89%. The identity of the reaction product was confirmed with $^1H$ and $^{13}C$ NMR. $^1H$-NMR: $\delta(COCl_3)$ 2.22(s,3H),2.27(s,3H),2.51(s,3H),3.81(s,3H),8.18(s,1H).

The reaction sequence is:

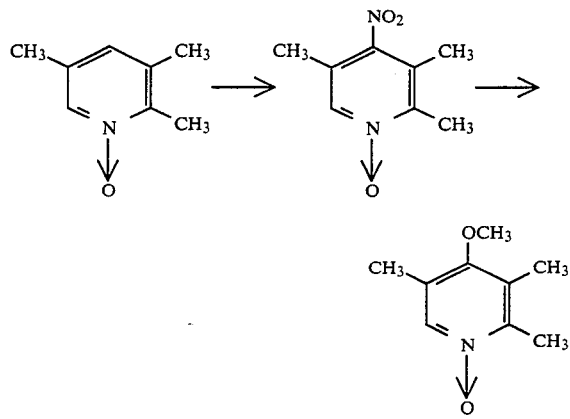

The 2,3,5-trimethylpyridine-N-oxide used as starting material was prepared as follows.

Preparation of 2,3,5-trimethyl-pyridine-N-oxide

To a 100 liters reaction vessel was added 2,3,5-trimethyl-pyridine (10.9 kg, 89.2 moles) and acetic acid (30 liters). The temperature was raised to 90° C. The mixture was stirred for 3 hours and thereafter cooled to 60° C., whereafter $H_2O_2$ (35% solution, 3122 ml, 35,67 moles) was added during 1 hour. The temperature was then raised to 90° C. The reaction mixture was stirred overnight. After cooling to 40° C. an additional amount of $H_2O_2$ solution (936 ml, 10.7 moles) was added during 1 hour. The temperature was then raised to 90° C. The reaction mixture was stirred for 3 hours and was allowed to stand without heating overnight. Excess of acetic acid was distilled off under vacuum. To the remainder was added NaOH (10M) until pH 10. $CH_2Cl_2$ (10 liters) was added and the resulting mixture was stirred vigorously. The $CH_2Cl_2$ phase was separated and the water phase was extracted twice with $CH_2Cl_2$ (10 liters). The combined $CH_2Cl_2$ - phases were dried over $MgSO_4$ and filtrated. The filtrate was evaporated yielding 2,3,5-trimethyl-pyridine-N-oxide (11920 g, 94% purity). The identity of the product was confirmed with $^1H$ and $^{13}C$ NMR.

EXAMPLE 2

Preparation of 3,5-dimethyl-4-methoxy-pyridine-N-oxide 3,5-dimethyl-pyridine-N-oxide (3500 g, 28.5 moles) was dissolved in conc. $H_2SO_4$ (3500 ml, 64.4 moles). The solution was cooled to 90° C. and nitration solution (5 l, 91.5 moles, conc. $H_2SO_4$ and 5.9 l, 85 moles 65% $HNO_3$) was added during 4 hours at 90° C. The solution was stirred at 90° C. over night. The solution was cooled to 30° C. and neutralized with 10M NaOH (36 l, 360 moles) during 4 hours and the temperature kept below 30° C. Acetonitrile (35 liters) was added and the mixture stirred vigorously for 30 minutes. The acetonitrile layer was separated. The extraction procedure was repeated with 15 l of acetonitrile, and the combined acetonitrile were extracted with water (10 l at 60° C.). The upper layer was collected and evaporated at reduced pressure (bp 30°–55° C./130 mm Hg). Toluene (10 l) was added and remaining water was thoroughly removed by azeotropic distillation at reduced pressure (bp 55°–65° C./130 mm Hg). Methylalcohol (7 l, 173 moles) was added and the mixture was heated to reflux temperature. A solution of NaOH (1138 g, 28.45 moles) in 30 liters methylalcohol was added over a period of 15 hours. The reaction mixture was cooled and pH adjusted to 9 using conc. HCl (1200 ml, 14 moles). Remaining methanol was evaporated. The residue was cooled and $CH_2Cl_2$ (30 l) and activated carbon (50 g) were added. The mixture was stirred for 30 minutes, filtered and the residue washed with $CH_2Cl_2$. The filtrates were evaporated. The solid product was washed with petroleum ether, (5 liters bp 60°–80° C.) at 50° C. for 30 minutes and filtered. This procedure was repeated once. The product was dried at reduced pressure. Yield 2400 g 3,5-dimethyl-4-methoxypyridine-N-oxide with a purity of 90%. The identity of the product was confirmed with $^1H$- and $^{13}C$-NMR. $^1H$-NMR: $\delta(COCl_3)$ 2.23(s,6H),3.81(2,3H), 8.03(s,2H).

The 3,5-dimethyl-pyridine-N-oxide used as starting material was prepared as follows.

3,5-lutidine (15 kg, 140.2 moles) was dissolved in acetic acid (48 l) at 60° C. Hydrogen peroxide (8430 ml, 98 moles) was added during 3 hours. The solution was heated to 90° C. and kept at this temperature for 3 hours. The reaction mixture was cooled to 60° C. and hydrogen peroxide (3500 ml, 41 moles) was added during 1 hour. The temperature was raised to 90° C. and kept there for 16 hours. The reaction mixture was evaporated at reduced pressure (70° C. 300 mm Hg). The residue (approx 25 liters) was cooled and pH adjusted to 10 with NaOH-solution (23 liters 10M). Acetonitrile (30 liters) was added and the mixture was stirred for 30 minutes. The sodiumacetate was separated off and washed with 10 l acetonitrile. The liquid phase was evaporated at reduced pressure (55° C., 200 mm Hg). The remaining solution (approx 25 liters) was extracted with $CH_2Cl_2$ (20 liters and 3×5 liters). The combined organic layers were dried over $MgSO_4$, filtrated and evaporated at reduced pressure (50° C. 200 mm Hg). When all $CH_2Cl_2$ had distilled off unreacted 3,5-lutidine was evaporated at 75° C., 8 mm Hg. Yield 14940 g of 3,5-dimethylpyridine-N-oxide. The identity was confirmed with $^1H$ and $^{13}C$ NMR.

The conversion of the compounds of the formula I to 3,5-dimethyl-4-methoxy-2-hydroxymethylpyridine can be carried out according to Procedure A and Procedure B as described above and exemplified below.

Procedure A step 1:

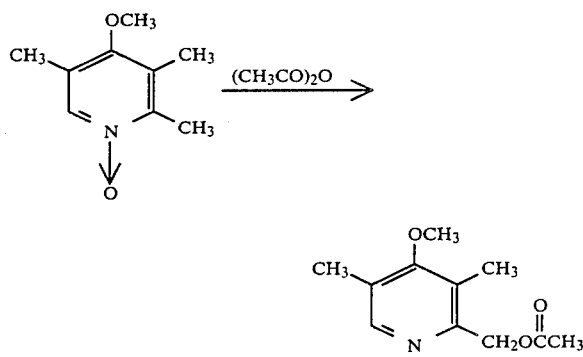

2,3,5-dimethyl-4-methoxypyridine-N-oxide (1268 g, 6.75 moles) obtained in Example 1, dissolved in acetic acid (740 ml), was added dropwise to $(CH_3CO)_2O$ (2140 ml) heated to 90° C. The heating was discontinued during the addition. The temperature rose to 130° C. Thereafter the reaction solution was stirred for 1 hour and then cooled to 80° C. whereafter $CH_3OH$ (2460 ml) was added. The reaction solution was evaporated and the remainder used directly in step 2.

step 2:

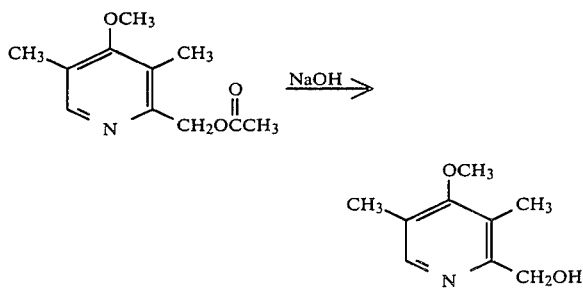

To the remainder from step 1 was added NaOH (3300 ml, 10M). The mixture was refluxed for 5 hours, cooled and extracted with $CH_2Cl_2$ (8 liters). The phases were separated and the water phase extracted with $CH_2Cl_2$ (2×4 liters). The combined $CH_2Cl_2$ - phases were dried over $MgSO_4$, refluxed with a few grams of decolorizing carbon and filtrated, yielding 3,5-dimethyl-4-methoxy-2-hydroxy-methylpyridine (941 g). The identity of the product was confirmed with $^1H$ and $^{13}C$ NMR.

Procedure B

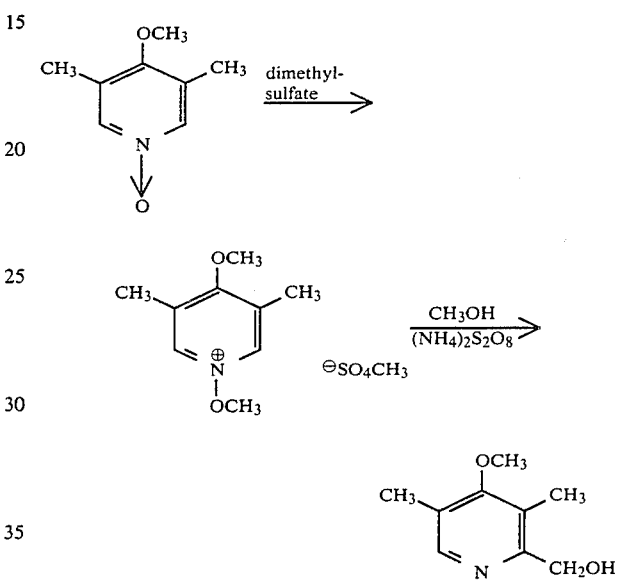

3.5-Dimethyl-4-methoxypyridine-N-oxide (61.2 g) obtained in Example 2 was dissolved in $CH_3OH$ (458 ml). Dimethylsulfate (38 ml 0.4 moles) was added dropwise during 15 minutes and pH adjusted to 5.0 using 10M NaOH. The mixture was stirred for 15 minutes and thereafter refluxed for 1 hour. An additional amount of dimethylsulfate (3.8 ml, 0.04 moles) was added dropwise and the mixture was refluxed for 1.5 hours. Stirring was continued overnight at room temperature. Thereafter the mixture was heated to reflux and $(NH_4)_2S_2O_8$ (91.2 g, 0.4 moles) dissolved in water (169 ml) was added during 1.75 hours, followed by refluxing for 1.5 hours and stirring at room temperature overnight. Thereafter $CH_3OH$ (452 ml) was added. Precipitated salts were filtered off and discarded. After evaporation of $CH_3OH$, the remaining water phase (pH 0.6) was adjusted to pH 10.0 using 10M NaOH (145 ml). The water phase was extracted three times with $CH_2Cl_2$. The combined $CH_2Cl_2$ phases were dried over $Na_2SO_4$, evaporated and dried, yielding 3,5-dimethyl-4-methoxy-2-hydroxymethylpyridine (44.2 g). The identity of the product was confirmed with $^1H$ and $^{13}C$ NMR and the purity checked with gas chromatography.

We claim:

1. A compound of the formula

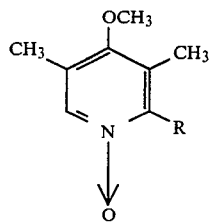
wherein R is H or CH₃.
2. The compound according to claim 1 of the formula
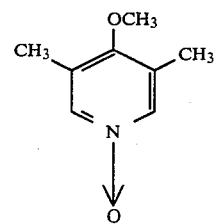
3. The compound according to claim 1 of the formula
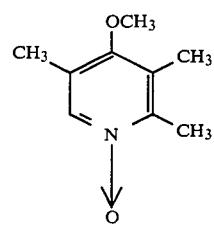
* * * * *